US010209202B1

(12) United States Patent
Sullivan et al.

(10) Patent No.: US 10,209,202 B1
(45) Date of Patent: Feb. 19, 2019

(54) OPTICAL CHARACTERIZATION SYSTEM FOR WIDE FIELD OF VIEW DIFFRACTIVE OPTICAL ELEMENTS

(71) Applicant: Facebook Technologies, LLC, Menlo Park, CA (US)

(72) Inventors: Mark Timothy Sullivan, Mountain View, CA (US); Andrew Matthew Bardagjy, Fremont, CA (US); Joseph Duggan, San Francisco, CA (US); Fei Liu, San Jose, CA (US); Simon Morris Shand Weiss, Redwood City, CA (US)

(73) Assignee: Facebook Technologies, LLC, Menlo Park, CA (US)

( * ) Notice: Subject to any disclaimer, the term of this patent is extended or adjusted under 35 U.S.C. 154(b) by 44 days.

(21) Appl. No.: 15/623,162

(22) Filed: Jun. 14, 2017

(51) Int. Cl.
*G06T 7/00* (2017.01)
*G01N 21/88* (2006.01)
*G01N 21/95* (2006.01)
*G06T 7/521* (2017.01)
*H04N 5/225* (2006.01)

(52) U.S. Cl.
CPC ......... *G01N 21/95* (2013.01); *G01N 21/8851* (2013.01); *G06T 7/521* (2017.01); *H04N 5/2256* (2013.01); *G01N 2021/9511* (2013.01); *G06T 7/0004* (2013.01); *G06T 2207/10028* (2013.01); *G06T 2207/30164* (2013.01); *G06T 2207/30244* (2013.01)

(58) Field of Classification Search
CPC ....... G01N 21/9036; G01N 2021/9511; G01N 21/95; G06T 7/521
See application file for complete search history.

(56) References Cited

U.S. PATENT DOCUMENTS

| 8,330,134 | B2* | 12/2012 | Yee | G01J 1/02 |
| | | | | 250/201.1 |
| 8,371,215 | B2* | 2/2013 | Rinko | B29C 59/02 |
| | | | | 101/27 |
| 9,063,001 | B2* | 6/2015 | Yee | G01J 1/02 |
| 9,256,943 | B2* | 2/2016 | Appia | G06T 7/0018 |
| 2003/0137655 | A1* | 7/2003 | Wegmann | G01M 11/0285 |
| | | | | 356/124 |

(Continued)

OTHER PUBLICATIONS

Paragios, N., Chen, Y., & Faugeras, O. (2006). Handbook of mathematical models in computer vision. New York: Springer. (Year: 2006).*

(Continued)

*Primary Examiner* — Jamie J Atala
*Assistant Examiner* — Michael Robert Cammarata
(74) *Attorney, Agent, or Firm* — Fenwick & West LLP (57) ABSTRACT

An optical characterization system includes a camera assembly and a workstation. The camera assembly is configured to capture images of different portions of a structured light pattern emitted from a device under test in accordance with imaging instructions. In some embodiments, the device under test may be a diffractive optical element (DOE). The workstation provides the imaging instructions to the camera assembly, and stitch the captured images together to form a pattern image. The pattern image is a single image of the entire structured light pattern. The workstation also characterizes performance of the device under test using the pattern image and a performance metric.

22 Claims, 4 Drawing Sheets

(56) References Cited

U.S. PATENT DOCUMENTS

| | | | | |
|---|---|---|---|---|
| 2005/0237540 A1* | 10/2005 | Ohkubo | ............... | G03F 7/706 |
| | | | | 356/515 |
| 2011/0062309 A1* | 3/2011 | Yee | ...................... | G01J 1/02 |
| | | | | 250/201.1 |
| 2011/0181688 A1* | 7/2011 | Miyamoto | ............ | G01B 15/04 |
| | | | | 348/36 |
| 2012/0304763 A1* | 12/2012 | Troxler | ............... | G01B 11/00 |
| | | | | 73/32 R |
| 2013/0056615 A1* | 3/2013 | Yee | ...................... | G01J 1/02 |
| | | | | 250/205 |
| 2015/0293038 A1* | 10/2015 | Orlov | ................. | G01N 21/87 |
| | | | | 356/128 |
| 2017/0256466 A1* | 9/2017 | Bishop | ................. | G06T 7/001 |
| 2017/0365060 A1* | 12/2017 | Ackley | ............... | H04N 5/225 |
| 2017/0371142 A1* | 12/2017 | Anthony | ........... | G02B 21/367 |

OTHER PUBLICATIONS

O'Shea Donald, C, Suleksi Thomas, J, Kathman Alan, D, & Prather Dennis, W 2010, Diffractive Optics—Design, , Fabrication, and Test, SPIE Chapter 9 Testing Diffractive Optical Elements. (Year: 2010).*

Ben-Hamadou, Achraf, Charles Soussen, Christian Daul, Walter Blondel, and Didier Wolf. 2013. "Flexible calibration of structured projecting point patterns." Computer Vision and Image Understanding 117, 1468-1481. (Year: 2013).*

C. Chen and A. Kak, "Modeling and calibration of a structure light scanner for 3-D robot vision," Proceedings. 1987 IEEE International Conference on Robotics and Automotion, Raleigh, NC, USA, 1987, pp. 807-815. (Year: 1987).*

* cited by examiner

OPTICAL CHARACTERIZATION SYSTEM FOR WIDE FIELD OF VIEW DIFFRACTIVE OPTICAL ELEMENTS

BACKGROUND

The present disclosure generally relates to characterization of optical elements, and specifically, to characterizing wide field of view diffractive optical elements.

In many cases, conventional depth camera systems use a diffractive optical element to generate a structured light pattern. The structured light pattern is then projected into a local area. The depth camera assembly then images the local area and uses the structured light in the image to determine depth for objects in the images. But, optical error has a tendency to increase as one moves further off-axis in the structured light pattern. In particular, in cases where the structured light pattern has a wide field of view (e.g., 150 degrees), optical aberrations (e.g., non-uniform brightness) can be significant. For example, brightness and/or distortion can vary depending with distance from the center of the structure light pattern. Conventional optical characterization systems do not exist to characterize devices that create structured light patterns over a wide field of view.

SUMMARY

An optical characterization system is used to characterize diffractive optical elements, and in some cases, wide field of view diffractive optical elements. The optical characterization system includes a camera assembly that captures one or more images of a structured light pattern emitted by device under test. The device under test may be, e.g., a diffractive optical element, a structured light projector, or some other device that generates a structured light pattern. In some embodiments, the camera assembly functions as a conoscope that measures an angular distribution of light emitted from the diffractive optical element under test. The structured light pattern may have a field of view that is larger than a field of view of the camera assembly. The camera assembly may capture images of different portions of a structured light pattern in accordance with imaging instructions.

The optical characterization system also includes a workstation. The workstation provides the imaging instructions to the camera assembly. The workstation uses images captured by the camera assembly to create a pattern image. A pattern image is a single image of the entire structured light pattern. In some embodiments, the workstation stitches the captured images together to form the pattern image. The stitching of multiple images into a pattern image of the entire structured light pattern allows the camera assembly to have a field of view that is potentially much smaller than that of the structured light pattern. Moreover, as the pattern image can cover fields of view much larger than the field of view of the camera assembly, it eases design constraints for the camera assembly. For example, it can be difficult and expensive to design/implement a camera system with minimal optical error that has a wide field of view (e.g., 180 degrees).

The workstation characterizes performance of the diffractive optical element under test using the pattern image and a performance metric (e.g., uniformity of brightness, astigmatism, comatic aberration, pincushion distortion, barrel distortion, etc.). Performance metrics are metrics used to determine qualities of the device under test as a function of angle and/or position. For example, the workstation may determine how uniform brightness is for the structured light pattern as a function of viewing angle. In some embodiments, the workstation generates a report. The report may compare one or more performance metrics to design data of the diffractive optical element. And the report may flag (e.g., highlight) any performance metrics that are out of specification. The report may be provided (e.g., via a monitor) to a user of the workstation.

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

DETAILED DESCRIPTION

System Overview

Figure 1:
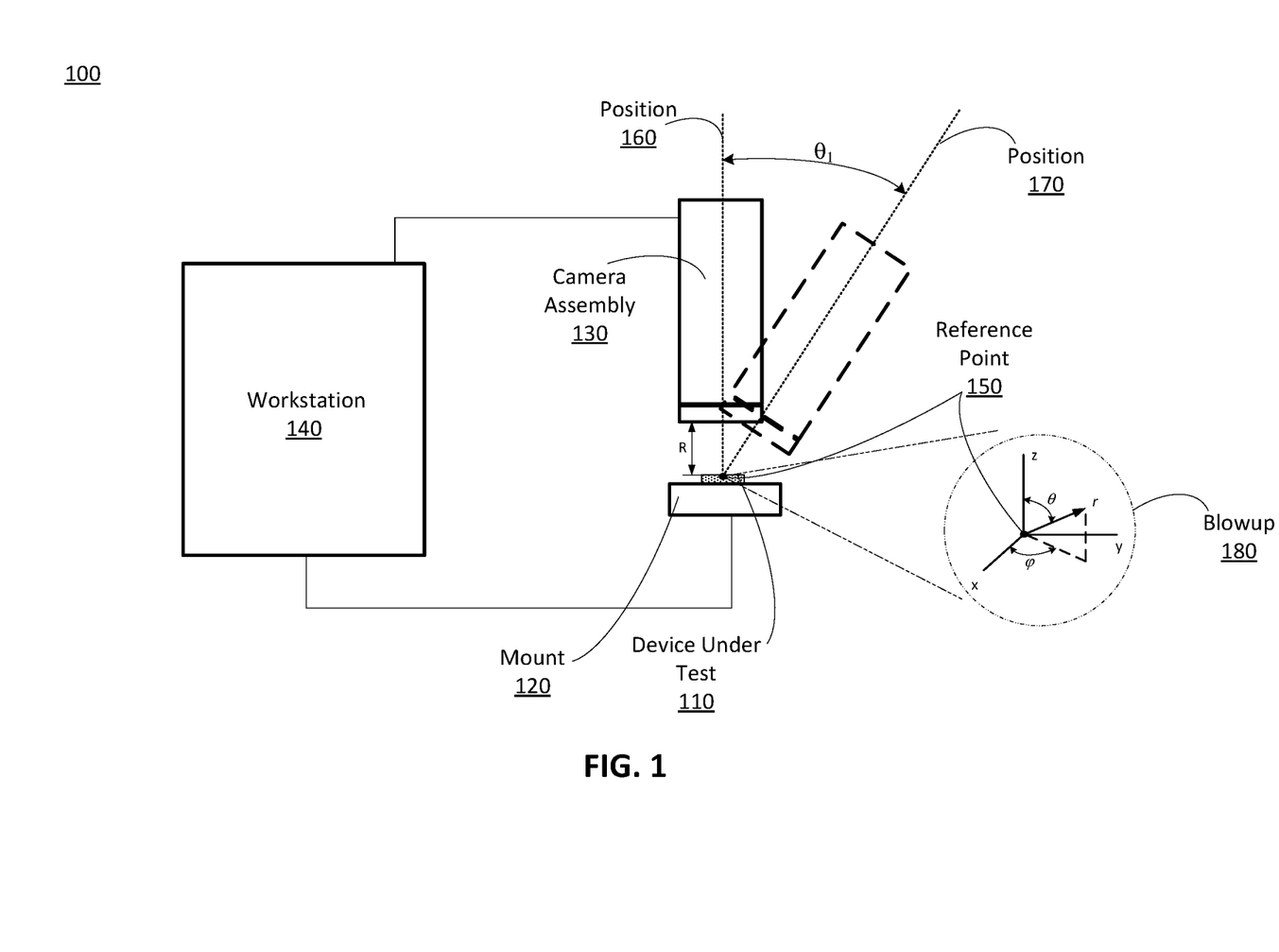
FIG. 1 is an example diagram of an optical characterization system characterizing a device under test, in accordance with an embodiment.

FIG. 1 is an example diagram of an optical characterization system 100 characterizing a device under test 110, in accordance with an embodiment. The optical characterization system 100 characterizes devices that produce structured light patterns. A device under test 110 may be, e.g., one or more diffractive optical elements (DOEs), a structured light projector, some other device that produces a structured light pattern, a diffuse illumination source, a diffuser, or some combination thereof. A DOE may be, e.g., a diffraction grating. A structured light projector includes at least a light source and a DOE, and may include additional optical elements. A diffuse illumination source includes at least a light source and diffuser. Characterization of a device under test 110 includes, e.g., generating as a function of position (translational and angle) one or more performance metrics applied to the structured light pattern produced by the device under test 110. The optical characterization system 100 includes a mount 120, a camera assembly 130, and a workstation 140. FIG. 1 shows merely one example and in alternative embodiments not shown, additional and/or different entities can be included in the optical characterization system 100. Likewise, functions performed by different entities in the optical characterization system 100 may differ in different embodiments.

In some embodiments, the device under test 110 generates a structured light pattern. In embodiments, where the device under test 110 is a DOE, the device under test 110 is illuminated with light that is diffracted by the DOE to generate the structured light pattern. In embodiments where the device under test 110 is a structured light projector, the structured light projector generates a structured light pattern in accordance with imaging instructions from the workstation 140. The structured light pattern may be a pattern of, e.g., dots, lines, sinusoids, diffuse light, some other feature used to determine depth measurements, or some combination thereof.

In some embodiments, the device under test 110 may generate a structured light pattern that has a wide field of view (WFOV). A WFOV may span, e.g., anywhere from 55 to 180 degrees. Conventional characterization systems do not exist for WFOVs.

The mount 120 holds the device under test 110. The optical characterization system 100 measures optical aberrations (e.g., non-uniform brightness) in the structured light pattern emitted by the device under test 110. The mount 120 couples the device under test 110 to a mounting area via a coupling assembly. The coupling assembly holds the device under test 110 to the mounting area. The coupling assembly may include, e.g., tabs, screws, mechanical arms, some other assembly that is configured to hold a device under test 110 in position, or some combination thereof. In some embodiments, the mount 120 may be configured to hold a wafer (e.g., including a plurality of DOEs and/or diffusors), a tray of optical elements, or both.

In some embodiments, the device under test 110 held by the mount 120 is fixed in place at the mounting area. In alternate embodiments, the mount 120 may be configured to adjust a position and/or orientation of the device under test 110 by one degree of freedom two degrees of freedom, three degrees of freedom, four degrees of freedom, five degrees of freedom, or six degrees of freedom in accordance with imaging instructions (provided by the workstation 140). For example the mounting area may be affixed to a mechanical stage that has up to six degrees of freedom. In some embodiments, the mount 120 may use feedback from the camera assembly 130 to tune a mechanical position of the device under test 110.

In some embodiments, the mount 110 includes a light source that can be used to illuminate the device under test 110 in accordance with the imaging instructions. In cases where the device under test 110 is a DOE, light incident on one side of the device under test 110 passes through and is diffracted by the device under test 110 to form a structured light pattern. In cases where the device under test 110 is a diffuser, light incident on one side of the device under test 100 passes through and is diffused by the device under test 110 to form diffuse illumination which is also referred to herein as a structured light pattern. The light source may emit light in a visible band, an infrared band, some other optical band, or some combination thereof. The light source may include, e.g., a laser diode, a laser, a tunable laser, or some other source that generates light having properties that enable the device under test 110 to generate a structured light pattern.

The camera assembly 130 captures some or all of the light pattern emitted by the device under test 110 in accordance with imaging instructions provided by the workstation 140. In some embodiments, the camera assembly 130 includes one or more cameras. In alternate embodiments, the camera assembly 130 includes different optical heads e.g., a camera, a power meter, an integrating sphere to measure total optical power, a beam profiler, a spectrometer to measure laser wavelength, some other optical head used to characterize the device under test 110, or some combination thereof. In some embodiments, the camera assembly 130 may automatically swap between different optical heads in accordance with the imaging instructions. Alternatively, a user of the optical characterization system 100 may mechanically swap the optical heads. In some embodiments, the camera assembly 130 may also include a positioning stage.

A camera may be, e.g., an array (1D or 2D) of photo-diodes, a charge coupled display (CCD) array, or some other device capable of detecting some or all of the structured light pattern. The one or more cameras act as a conoscope that measures an angular distribution of light emitted from the device under test 110. Moreover, as the camera assembly 130 may be scanned (as discussed below) it functionally can act as a wide field of view conoscope. The camera assembly 130 precisely maps incoming angles to positions on a captured image. This means that if, e.g., two objects are separated by 5°, they will be mapped to, say, 50 pixels apart, regardless of where they are in a field of view of the camera assembly 130.

The camera assembly 130 has a field of view over which it can capture images of the light emitted by the device under test 110. The field of view of the camera assembly 130 is at least a 90 degree diagonal field of view, and can have other larger field of views (e.g., 130 degrees diagonal field of view). In some cases the field of view of the camera assembly is less, and sometimes, much less than a field of view of the structured light pattern generated by the device under test 110. The camera assembly 130 captures different images of the structured light pattern from different positions relative to the device under test 110 in accordance with imaging instructions. As is discussed below in detail, the captured images can be stitched together to from a single image of the entire structured light pattern (also referred to as a pattern image). The change in position is relative to a reference point 150. In some embodiments, the reference point 150 may be located at, e.g., a top surface of the device under test 110. For example, an exposed surface that emits the structured light pattern from the device under test 110. In alternate embodiments, the reference point 150 may be located elsewhere, e.g., on a surface of the mount 120.

In some embodiments, the camera assembly 130 may be configured to adjust a position and/or orientation of the camera assembly 130 relative to the device under test 110 and/or the reference point 150 by one degree of freedom two degrees of freedom, three degrees of freedom, four degrees of freedom, five degrees of freedom, or six degrees of freedom in accordance with imaging instructions (provided by the workstation 140). To help illustrate this point a blowup 180 of a coordinate system placed at the reference point 150 is illustrated in FIG. 1. Note that a relationship between Cartesian coordinate system and a spherical coordinate system ($r$, $\theta$, $\varphi$) is shown in an isometric view. In the illustrated embodiment, the reference point 150 is at a vertex of the coordinate system, a top surface of the device under test 110 resides in an x-y plane, and a z-axis runs axially through the camera assembly 130 in a position 160. The parameter r is a distance from the reference point 150 to an outside surface of an objective lens of the camera assembly 130. In some embodiments, a distance between the objective lens and the reference point is no more than 5 mm, and can be less than 1 mm. Accordingly, in some embodiments, the camera assembly 130 for a given value of r (e.g., 5 mm) and various values of $\theta$ and $\varphi$ can capture images of portions of the structured light pattern that together can be stitched together to form a pattern image of the entire structured light pattern. The camera assembly 130 selects values for r, $\theta$, and $\varphi$ in accordance with the imaging instructions. For simplicity only two positions of the camera assembly 130 are illustrated in FIG. 1, position 160 and position 170. However, the relative positioning between the camera assembly and the device under test 110 can range over r, $\theta$, and $\varphi$ such that the camera assembly 130 is able to capture images of the entire structured light pattern or portions of the structured light pattern that can be stitched together to form a pattern image.

Note, that to ease optical design requirements of the camera assembly 130, the camera assembly 130 can be placed relatively close to the device under test 110. A small value of r (on the order of millimeters) helps, e.g., mitigate vignetting, having a very large objective lens of the camera assembly 130, etc. While a small r value can limit the field of view of the camera assembly 130, this limitation is offset by the ability of the optical characterization system 100 to capture images of different portions of the structured light pattern and later stich them together to form a pattern image of the entire structured light pattern.

The workstation 140 is a computer that controls components in the optical characterization system 100. The workstation 140 generates imaging instructions and provides them to the camera assembly 130 and/or the mount 120. The workstation 140 generates a pattern image using images captured of the structured light pattern by the camera assembly 130. The workstation 140 characterizes the device under test 110 using the pattern image. Operation of the workstation 140 is described in detail below with regard to FIG. 2.

Figure 2:
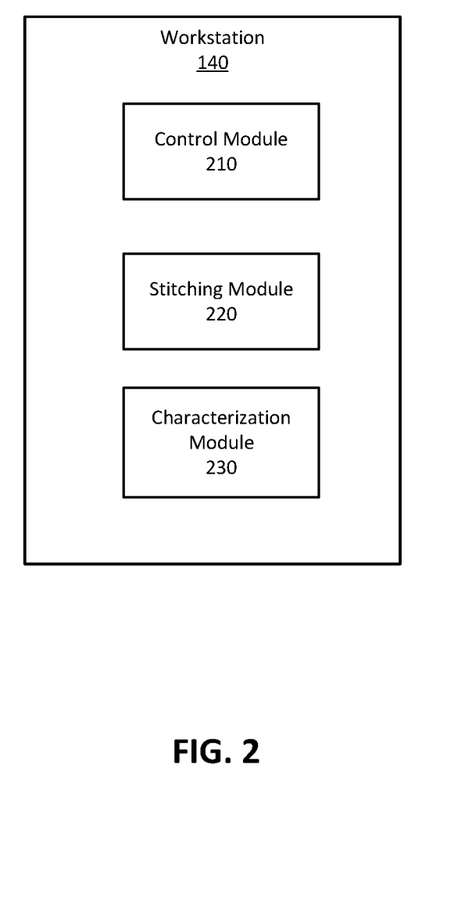
FIG. 2 is a block diagram of a workstation of the optical characterization system of FIG. 1, in accordance with an embodiment.

FIG. 2 is a block diagram of the workstation 140 of the optical characterization system 100 of FIG. 1, in accordance with an embodiment. The workstation 140 includes a control module 210, a stitching module 220, and a characterization module 230. FIG. 2 shows merely one example and in alternative embodiments not shown, additional and/or different modules can be included in the workstation 140. Likewise, functions performed by different modules in the workstation 140 may differ in different embodiments.

The control module 210 controls other components of the optical characterization system 100. The control module 210 controls the device under test 110, the mount 120, the camera system 130, or some combination thereof. The control module 210 receives input parameters. Input parameters control the characterization process of the device under test 110. Input parameters may include, e.g., source wavelength, field of view of a structured light pattern emitted by the device under test 110, a number of images per position, performance metric (e.g., modulation transfer function, astigmatism, distortion, pattern contrast, zero-order power, illumination uniformity, wavelength, optical power, etc.) for test, device under test data (e.g., field of view), frame capture rate, frame integration time, relative positioning information, some other parameter that controls the characterization of the device under test 110, or some combination thereof. A user of the optical characterization system 100 or the optical characterization system 100 itself may provide and/or generate one or more of the input parameters. And a user of the optical characterization system 100 or the optical characterization system 100 itself may determine an optical head based on one or more of the input parameters (e.g., selects a spectrometer if want to measure wavelength).

Relative positioning information is information controlling a position of the camera assembly 130 and/or the mount 120 such to control a relative position of the camera assembly 130 to the mount 120 and the device under test 110. Relative positioning information may include, e.g., a plurality of positions for the camera assembly 130 and/or the mount 120 such that the camera assembly 130 is able to capture images that can be stitched together to form a pattern image of the entire structured light pattern emitted by the device under test 110.

In some embodiments, the control module 210 determines relative position information based on one or more of the input parameters. For example, the control module 210 may determine a projected field of view of the structured light pattern. A projected field of view is the structured light pattern projected onto a surface (e.g., sensor surface) at a plane of the camera assembly 130. The control module 210 then compares the projected field of view with a field of view of the camera assembly 130 to determine whether the camera assembly 130 has a field of view sufficiently large to capture the entire projected field of view. In cases where the device under test 110 has a field of view that is larger than the field of view of the camera assembly 130, the control module 210 divides the projected field of view of the structured light pattern into portions. And the portions are individually at most the size of the field of view of the camera assembly 130. The control module 210 then determines relative position information for the mount 110 and/or the camera assembly 130 such that the camera assembly 130 can capture images of each of the portions of the structured light pattern. The control module 210 generates the imaging instructions using one or more of the input parameters. The imaging instructions control operation of device under test 110, the mount 120, the camera system 130, or some combination thereof. The control module 210 provides the imaging instructions to the device under test 110, the mount 120, the camera system 130, or some combination thereof.

The stitching module 220 stitches a plurality of captured images of different portions of a structured light pattern into a pattern image of the entire structured light pattern. In some embodiments, the stitching module 220 utilizes the imaging instructions, and in particular, the relative position information, to identify locations of each captured image in the structured light pattern, and then combines the plurality of images into a single pattern image of the entire structured light pattern. In some embodiments, the stitching module 220 identifies a number of images from different poses that are overlapping (e.g., 10-30% overlap). The stitching module 220 identifies features in each of those images. Those features have some "descriptor" be it a small patch, some multi-scale feature, a unique local histogram, and/or some color or texture, and the stitching module 220 matches the descriptors across images to form correspondences. The stitching module 220 tests those correspondences against a pose hypothesis given some projection between the images (e.g., affine, perspective). The stitching module 220 discards the outlier correspondences, and those pose hypotheses are used to project the images onto a common embedding (e.g., cylinder, sphere, plane).

The characterization module 230 characterizes performance of the device under test using the pattern image and a performance metric. Note that the structured light pattern is composed of a plurality of features (e.g., a dot, a line, etc.). The characterization module 230 identifies optical aberrations in the structured light pattern (e.g., observed in structured light features) emitted by the device under test 110. The characterization module 230 analyzes the identified optical aberrations using one or more performance metrics. Performance metrics are metrics used by the optical characterization system 100 to determine qualities of the device under test 110 as a function of angle and/or position, and example performance metrics can include: uniformity of brightness of the structured light features, astigmatism, comatic aberration, pincushion distortion, barrel distortion, shape of the structured light features, and location of the structured light features, etc. For example, in a device under test 110 having a WFOV (e.g., 170 degrees) brightness may be less near a periphery of a structured light pattern than near its center. The characterization module 230 can identify the brightness of each structured light feature relative to each other using the pattern image to determine how brightness changes with angle (θ, φ) for a given value of r.

In some embodiments, the characterization module 230 generates a report including an optical profile of the device under test 110. In some embodiments, the report may compare one or more performance metrics to design data of the device under test 110 (e.g., provided by a manufacturer of the DOE and/or structured light projector). And the report may flag (e.g., highlight) any performance metrics that are out of specification. The report may be provided (e.g., via a monitor) to a user of the workstation 140.

Figure 3:
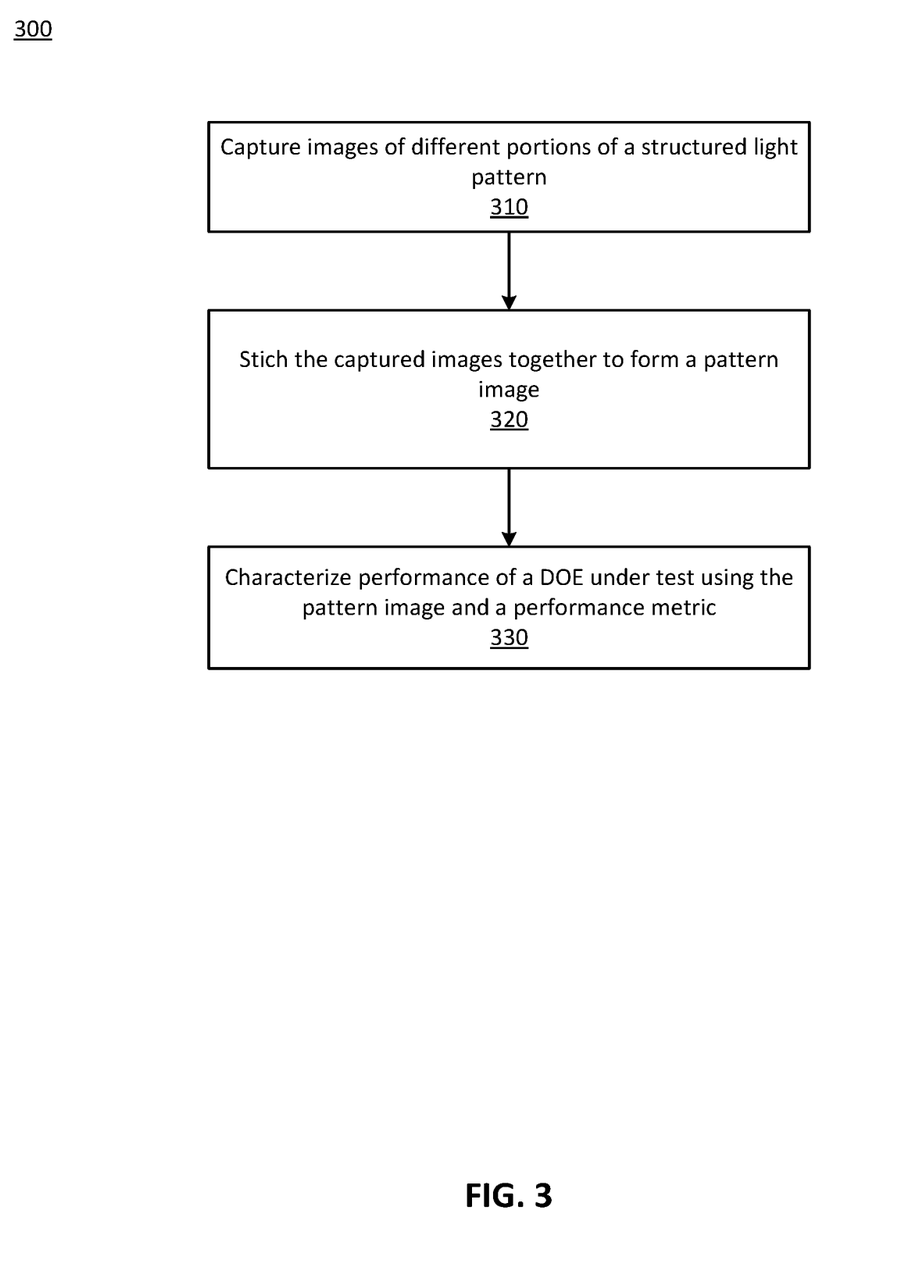
FIG. 3 is a flow chart of an example process for characterizing a device under test, accordance with an embodiment.

FIG. 3 is a flow chart of an example process 300 for characterizing a device under test 110 in accordance with an embodiment. The process 300 of FIG. 3 may be performed by an optical characterization system 100. Other entities may perform some or all of the steps of the process in other embodiments. Likewise, embodiments may include different and/or additional steps, or perform the steps in different orders.

The optical characterization system 100 captures 310 images of different portions of a structured light pattern. The structured light pattern is generated by a device under test (e.g., the device under test 110). The device under test may be, e.g., a DOE illuminated with laser light to form a structured light pattern over a wide field of view (e.g., over 55 degrees). The optical characterization system 100 determines relative positioning of a camera assembly (e.g., the camera assembly 130) relative to the device under test to capture images of the structured light pattern. In cases where a field of view of the camera is large enough to capture the entire structured light pattern, then a single relative of the camera assembly to the device under test may be used. In cases where the field of view of the camera assembly is not large enough to capture the entire structured light pattern, the optical characterization system 100 determines relative positioning information controlling a relative position of the camera assembly 130 to the mount 120 and the device under test 110. As discussed above with regard to FIG. 2, the relative positioning information identifies positions of the camera assembly and/or mount such that the camera assembly can capture images of different portions of the structure light pattern that together can be stitched together to form a pattern image of the entire structured light pattern. The optical characterization system 100 then captures images of the structured light pattern (or portions thereof) in accordance with the determining relative positioning information.

The optical characterization system 100 stitches 320 the captured images together to form a pattern image. The pattern image is an image of the entire structured light pattern. The optical characterization system 100 uses the imaging instructions, and in particular, the relative position information, to identify locations of each captured image in the structured light pattern, and then combines the plurality of images into a single pattern image of the entire structured light pattern. Combining the plurality of images into a single pattern image of the projected pattern enables characterization of a very wide field of view projected pattern (e.g., 170 degrees) using a camera assembly with a narrower field of view.

The optical characterization system 100 characterizes 330 performance of a device under test (e.g., the device under test 110) using the pattern image and a performance metric. The optical characterization system 100 analyzes the pattern image to determine one or more performance metrics (MTF, astigmatism, distortion, etc.). As noted above the performance metrics may be a function of angle (e.g., distance from the center). Additionally, in some embodiments, the optical characterization system 100 may generate a report describing the optical profile and provide it to the user. Additionally, the report may highlight any areas where the device under test does not meet specification.

Note, that the above embodiment describes a case where the field of view of the camera assembly is not large enough to capture the entire structured light pattern. In alternate embodiments, where the field of view of the camera assembly is large enough to capture the entire structured light pattern, the process flow 300 is slightly different. For example, at least one image may be captured, and the at least one image may be used to characterize 330 the device under test.

Depth Camera Assembly Overview

Figure 4:
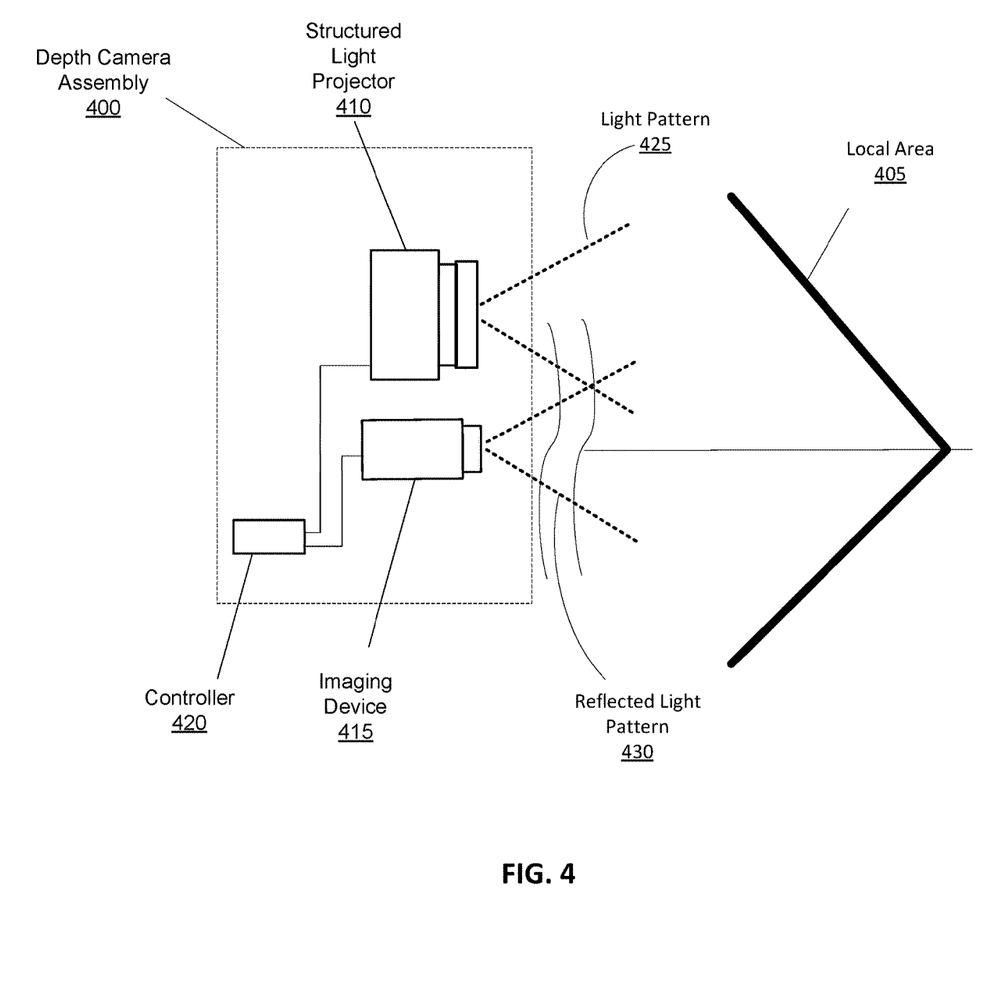
FIG. 4 is a diagram of a depth camera assembly, in accordance with an embodiment.

FIG. 4 is an example depth camera assembly (DCA) 400 configured for depth sensing, in accordance with an embodiment. In some embodiments, the DCA 400 may be incorporated into a system that uses depth information for objects in a local area (e.g., a head-mounted display (HMD) for VR applications). The DCA 400 may be configured to determine depth information of one or more objects in a local area 405 surrounding some or all of the DCA 400. The DCA 400 includes a structured light projector 410, an imaging device 415, and a controller 420 that may be coupled to both the structured light projector 410 and the imaging device 415. The structured light projector 410 illuminates the local area 405 with a light pattern 425 in accordance with emission instructions generated by the controller 420. The light pattern 425 may be a structured light pattern (e.g., dot pattern).

The structured light projector 410 may include one or more emitters that each emit light having certain characteristics (e.g., wavelength, polarization, coherence, pulse width, temporal behavior, etc.). The characteristics may be the same or different between emitters, and the emitters can be operated simultaneously or individually. An emitted may be, e.g., laser diodes (e.g., edge emitters), inorganic or organic LEDs, a vertical-cavity surface-emitting laser (VCSEL), or some other source. The one or emitters illuminate one or more DOEs, and the one or more DOEs generate a structured light pattern that is projected into the local area 405. In some embodiments, at least one DOE of the one or more DOEs generates structured light over a wide field of view (e.g., 55 to 180 degrees).

The imaging device 415 is configured to capture portions of a light pattern 430 reflected from the local area 405. The imaging device 415 may include a charge-coupled device (CCD) detector, a complementary metal-oxide-semiconductor (CMOS) detector or some other types of detectors (not shown in FIG. 1). The imaging device 415 captures, e.g., via a detector, one or more images of one or more objects in the local area 405 illuminated with the light pattern 425.

The controller 420 controls operation of certain components of the structured light projector 410, based on the emission instructions. In some embodiments, the controller 420 may provide the emission instructions to one or more optical elements (not shown in FIG. 4) within the structured light projector 410 to control a field-of-view of the local area 405 illuminated by the light pattern 425.

The controller 420 is configured to determine depth information for one or more objects in the local area 405 based at least in part on the captured portions of the reflected light pattern 430. In some embodiments, the controller 420 is configured to determine depth information based on phase-shifted patterns of the portions of the reflected light pattern 430 distorted by shapes of the one or more objects in the local area 405, and to use triangulation calculation to obtain a depth map of the local area 405. In some embodiments, the controller 420 provides the determined depth information to a console (not shown in FIG. 4) and/or a HMD (not shown in FIG. 1). The console and/or the HMD may utilize the depth information to, e.g., generate content for presentation to a user on an electronic display of the HMD.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. An optical characterization system comprising:
   a camera assembly including a plurality of optical heads, the optical heads including a camera and an integrating sphere, the camera assembly configured to measure different portions of a structured light pattern in accordance with imaging instructions, the structured light pattern generated by a diffractive optical element (DOE) under test, and the structured light pattern having a field of view that is larger than a field of view of the camera assembly, and each measured different portion of the structured light pattern is captured at a same radial distance from a reference point on the DOE under test; and
   a workstation configured to:
      provide the imaging instructions to the camera assembly, the imaging instructions causing the camera assembly to use the camera head to capture images of the different portions of the structured light pattern,
      stitch the captured images together to form a pattern image, wherein the pattern image is a single image of the entire structured light pattern, and
      characterize performance of the DOE under test using the pattern image and a performance metric.

2. The system of claim 1, further comprising:
   a mount coupled to the DOE under test, the mount comprising a light source assembly that is configured to illuminate the DOE under test to generate the structured light pattern.

3. The system of claim 1, wherein the DOE under test is part of a structured light projector, the structured light projector including one or more emitters that are configured to illuminate the DOE under test to generate the structured light pattern.

4. The system of claim 1, wherein the same radial distance is no more than 5 mm.

5. The system of claim 1, wherein the workstation is further configured to:
   divide a projected field of view of the structured light pattern into portions, where each portion has a projected field of view that corresponds to at most the field of view of the camera;
   determine relative position information describing a relative position of the camera assembly to the DOE under test for each of the portions; and
   generate the imaging instructions using the relative position information.

6. The system of claim 5, further comprising:
   a mount coupled to the DOE under test, the mount configured to adjust a position of the DOE under test relative to the camera assembly in accordance with the imaging instructions.

7. The system of claim 5, wherein the camera assembly is configured to adjust its position relative to the DOE under test in accordance with the imaging instructions.

8. The system of claim 1, wherein the structured light pattern includes a plurality of structured light features, and the workstation is further configured to:
   analyze structured light features in the pattern image using the performance metric;
   generate a report based on the analysis; and
   present the report.

9. The system of claim 8, wherein the performance metric is selected from a group consisting of: astigmatism, comatic aberration, pincushion distortion, barrel distortion, uniformity of brightness of the structured light feature, shape of the structured light features, and location of the structured light features.

10. The system of claim 1, wherein the camera assembly is a conoscope, and incoming angles of the structured light are mapped to positions on the single image.

11. The system of claim 1, wherein the camera assembly has at least three degrees of freedom and can change position over r, θ, and φ, wherein r is a radial distance from the reference point to the camera assembly, θ is a polar angle, and φ is an azimuthal angle in a spherical coordinate system whose origin is at the reference point.

12. The system of claim 1, wherein the imaging instructions also cause the camera assembly to change from a first optical head to a second optical head, wherein the first optical head is the integrating sphere, and the second optical head is the camera.

13. A method comprising:
measuring, by a camera assembly including a plurality of optical heads that include a camera and an integrating sphere, different portions of a structured light pattern in accordance with imaging instructions, the structured light pattern generated by a diffractive optical element (DOE) under test, and the structured light pattern having a field of view that is larger than a field of view of the camera assembly, and each measured different portion of the structured light pattern is captured at a same radial distance from a reference point on the DOE under test, wherein the imaging instructions cause the camera assembly to use the camera head to capture images and each measured portion is an image of a different portion of the structured light pattern;
stitching the captured images together to form a pattern image, wherein the pattern image is a single image of the entire structured light pattern; and
characterizing performance of the DOE under test using the pattern image and a performance metric.

14. The method of claim 13, further comprising:
illuminating the DOE under test with light to generate the structured light pattern.

15. The method of claim 13, wherein the same radial distance is no more than 5 mm.

16. The method of claim 13, further comprising:
dividing a projected field of view of the structured light pattern into portions, where each portion has a projected field of view that corresponds to at most the field of view of the camera;
determining relative position information describing a relative position of the camera assembly to the DOE under test for each of the portions; and
generating the imaging instructions using the relative position information.

17. The method of claim 16, wherein capturing, by the camera assembly, images of different portions of a structured light pattern in accordance with imaging instructions, further comprises:

adjusting via a mount coupled to the DOE under test a position of the DOE under test relative to the camera assembly in accordance with the imaging instructions.

18. The method of claim 13, wherein the structured light pattern includes a plurality of structured light features, and characterizing performance of the DOE under test using the pattern image and the performance metric further comprises:
analyzing structured light features in the pattern using the performance metric;
generating a report based on the analysis; and
presenting the report.

19. The method of claim 18, wherein the performance metric is selected from a group consisting of: astigmatism, comatic aberration, pincushion distortion, barrel distortion, uniformity of brightness of the structured light feature, shape of the structured light features, and location of the structured light features.

20. The method of claim 13, wherein the camera assembly is a conoscope, and incoming angles of the structured light are mapped to positions on the single image.

21. A non-transitory computer-readable storage medium storing executable computer program instructions, the instructions executable to perform steps comprising
measuring, by a camera assembly including a plurality of optical heads that include a camera and an integrating sphere, different portions of a structured light pattern in accordance with imaging instructions, the structured light pattern generated by a diffractive optical element (DOE) under test, and the structured light pattern having a field of view that is larger than a field of view of the camera assembly, and each measured different portion of the structured light pattern is captured at a same radial distance from a reference point on the DOE under test, wherein the imaging instructions cause the camera assembly to use the camera head to capture images and each measured portion is an image of a different portion of the structured light pattern;
stitching the captured images together to form a pattern image, wherein the pattern image is a single image of the entire structured light pattern, and
characterizing performance of the DOE under test using the pattern image and a performance metric.

22. The computer-readable medium of claim 21, further comprising:
dividing a projected field of view of the structured light pattern into portions, where each portion has a projected field of view that corresponds to the field of view of the camera;
determining relative position information describing a relative position of the camera assembly to the DOE under test for each of the portions; and
generating the imaging instructions using the relative position information.

* * * * *

UNITED STATES PATENT AND TRADEMARK OFFICE
CERTIFICATE OF CORRECTION

PATENT NO. : 10,209,202 B1
APPLICATION NO. : 15/623162
DATED : February 19, 2019
INVENTOR(S) : Mark Timothy Sullivan et al.

It is certified that error appears in the above-identified patent and that said Letters Patent is hereby corrected as shown below:

On the Title Page

Item (57) Abstract, delete "The workstation provides the imaging instructions to the camera assembly, and stitch the captured images" and insert -- The workstation provides the imaging instructions to the camera assembly, and stitches the captured images --

Signed and Sealed this
Twenty-fifth Day of June, 2019

Andrei Iancu
*Director of the United States Patent and Trademark Office*